United States Patent [19]
Alt et al.

[11] Patent Number: 5,725,559
[45] Date of Patent: Mar. 10, 1998

[54] PROGRAMMABLY UPGRADABLE IMPLANTABLE MEDICAL DEVICE

[75] Inventors: Eckhard Alt, Ottobrunn, Germany; Lawrence J. Stotts, Lake Jackson, Tex.

[73] Assignee: Intermedics Inc., Angleton, Tex.

[21] Appl. No.: 648,707

[22] Filed: May 16, 1996

[51] Int. Cl.⁶ ................................................ A61N 1/39
[52] U.S. Cl. .......................... 607/5; 607/31; 607/59; 128/903
[58] Field of Search ................... 607/5, 30–32, 607/59, 60; 128/903

[56] References Cited

U.S. PATENT DOCUMENTS

| | | |
|---|---|---|
| 4,404,972 | 9/1983 | Borkan . |
| 4,459,989 | 7/1984 | Borkan . |
| 4,613,937 | 9/1986 | Batty, Jr. .................... 607/31 X |
| 5,311,449 | 5/1994 | Adams ........................ 607/9 X |
| 5,360,437 | 11/1994 | Thompson . |
| 5,383,909 | 1/1995 | Keimel ........................ 607/7 |
| 5,391,194 | 2/1995 | Goldreyer .................... 607/31 |
| 5,439,481 | 8/1995 | Adams ........................ 607/5 |
| 5,456,692 | 10/1995 | Smith, Jr. et al. .......... 607/31 |
| 5,509,927 | 4/1996 | Epstein et al. .............. 607/32 |

*Primary Examiner*—Jeffrey R. Jastrzab
*Attorney, Agent, or Firm*—Wigman Cohen Leitner & Myers P.C.

[57] ABSTRACT

An implantable cardioverter/defibrillator device is implemented to be selectively non-invasively upgraded from time to time after implantation to enable the device to provide additional therapy for arrhythmia treatment as the patient's need for such treatment undergoes change. The device is adapted to provide a plurality of functions corresponding to different levels of therapy for treating arrhythmias, and to respond to each different type of arrhythmia that may be sensed, to supply a function which is designated as being appropriate to relieve that respective arrhythmia. Each function is not necessarily unique to treating a particular arrhythmia, and, in at least some instances, may be used to treat more than one of the plurality of different types of arrhythmias. At the time of its implant, the device is restricted from providing those of the plurality of functions which are deemed as being non-essential to the patient's needs at that time. From time to time thereafter, however, as the patient experiences periodic need for additional therapy, restricted functions of the device are selectively restored by external programming, but only if the programmer is able to supply to the device an enabling code which is substantially unique to that device. In this way, restoration of the restricted functions is locked out except with a prescribed key.

16 Claims, 3 Drawing Sheets

PROGRAMMABLY UPGRADABLE IMPLANTABLE MEDICAL DEVICE

BACKGROUND OF THE INVENTION

The present invention relates generally to implantable medical devices, and more particularly to such devices which are adapted for a capability to be upgraded or modified non-invasively while surgically implanted, through remote programming.

Improvements in implantable medical devices and their components in recent years have enabled significant reduction in size and weight of the device to be implanted. In particular, the use of many developments that previously constituted advances in cardiac pacemakers have led to reductions in size and weight of implantable defibrillators. From a typical volume of about 160 cubic centimeters (cc) and weight of 280 grams (g) only about six years ago, current figures are about 80 cc and about 130 g, respectively. Further weight reduction to less than 100 grams is foreseeable, with concomitant reduction in volume.

Principally because of these improvements in the physical characteristics of the implantable defibrillator device, an accompanying significant reduction in the complexity of its implant procedure has been achieved. Through the early 1990's it remained customary to perform defibrillator implants by a thoracotomy procedure, with application of two epicardial patches to the heart, followed by implantation of additional sensing leads. More recently, the technique of non-thoracotomy implantation has reduced the complexity of the procedure considerably. Published data of Sakseena et al in the *Journal of the American College of Cardiology* (JACC) in 1994, and of Ducsives in *Circulation* in 1995, compare results using epicardial patch devices with those using non-thoracotomy devices. From experience with several hundred patients in both groups, a highly significant reduction in morbidity and mortality is seen from the data, for patients with non-thoracotomy implants. Similar data compiled by Nisam of Cardiac Pacemakers, Inc. (CPI), published in *PACE* in 1995 shows a dramatic reduction in one year mortality with such implants, from 12% to only 7%.

Part of this reduction is attributable to the decrease in mortality during the operation itself, on average from about 4% to a figure below 1% for non-thoracotomy implants. Additionally, reduction of morbidity from infection, pericardial effusion, pneumothorax, and other factors, have led to an increased survival rate. Therefore, implantation of a defibrillator, with its increased benefit-to-risk ratio, no longer constitutes the ominous decision it once held for a patient with very high risk of sudden cardiac death. For the same reasons, the number of patients for whom defibrillator implantation is an electable procedure is constantly increasing.

Reduction in size and weight of implantable defibrillators has allowed not only non-thoracotomy procedures, such as pectoral implants, but has led to the use of the defibrillator shell or case (often referred to in the art as the "can") as one pole for the defibrillation pathway. This has reduced the number of leads required to be implanted in the patient. Accordingly, this implant procedure is no longer the domain solely of cardiac thoracic surgeons, but is being practiced by an increasing number of cardiologists. With further weight reduction of the device to the range of 85 to 90 grams, which is currently in the planning stage of many device manufacturers, a subcutaneous implant will be available.

This augers a continuous increase in the number of doctors and medical centers through which such procedures will be available.

A widespread need exists for this therapy. More than 250,000 persons in the United States and more than 100,000 in Germany, for example, suffer sudden cardiac death each year. For some, the occurrence of this lethal event is not predictable, but in many others, certain mechanisms or characteristics are identifiable by which to predict the patient at high risk. By combining several parameters such as left ventricular ejection fraction, results from Holter monitoring, results from electrophysiology studies, late potentials in the electrocardiogram (EKG, or ECG), and heart rate variability, to name a few, the medical community is in a good position to identify prime candidates for implant therapy. This is true despite the low relative specificity, and thus reduced predictability, afforded by any single one of these parameters, and regardless of their individual high sensitivity. In effect, this means that although candidates for acute sudden cardiac death may be predicted with an accuracy of 50% or slightly more, only one of every two defibrillator implants will be effective to save a life.

Despite advances in the devices themselves, in the surgical procedures for implanting the devices, in the ability to identify prime candidates for such implants, and the enhancement of the quality of life and survival rates for implant patients, it is a hard fact that no socio-economic society has been developed that is capable of bearing the cost to provide this therapy to all of the potential candidates for the procedure.

SUMMARY OF THE INVENTION

It is a principal aim of the present invention is to enable the benefits of this life-saving therapeutic device to be made available to a larger number of patients than would otherwise be provided with this option. To that end, the invention maintains the costs of the device and related implant procedures at a relatively reasonable level by limiting the device to the minimum primary life saving capabilities needed by the patient for current therapy.

Further, the implant is adapted to be upgradable, at additional cost, to allow the patient to receive the benefit of improved features or parameters of the device when, if, and as needed by the patient. This means, in essence, that the patient need not face another surgical procedure in order to receive a new device or additional device capabilities, but may have the current implanted device upgraded to provide the required features in a non-invasive manner, and at a fraction of the cost of a new implant. Moreover, although the risks of surgery to implant these devices have been drastically reduced in recent years, as pointed out above, nevertheless there remains a risk anytime this type of surgery is performed, so that the patient receives an additional benefit if he or she need only be subjected to a non-invasive procedure to enable available but otherwise dormant features to be implemented.

According to a preferred embodiment of the invention, a solution to the problem is effected by providing a basic implantable defibrillator which—although it may be and preferably is capable of providing a variety of different cardiac arrhythmia or dysrhythmia therapies—for purposes of this summary is considered (at least initially) merely from the standpoint of its capability to deliver an electrical waveform defibrillating shock to the patient's heart (characterized herein as a "shock"). The shock, which is of predetermined appropriate current and voltage field gradient, is derived from the discharge of a capacitor in the device whose charging was commenced at the time that fibrillation was first sensed. Ideally, delivery of this shock to the heart will be effective to defibrillate the heart and return the heart rate to normal sinus rhythm.

In the case of most cardiac patients, the conditions sought to be treated by the implant may not consist only of fibrillation. For example, in most patients with ventricular fibrillation, ventricular tachycardia may be experienced before fibrillation occurs that could, for an earlier episode, have been broken by antitachycardia cardiac stimulation or by automatic delivery of antitachycardia pacing pulses, but as a result of advanced disease of the patient, now requires a more rigorous, aggressive, or even adjunct therapy, such as VVIR rate adaptive pacing in order to improve an underlying cardiac hemodynamic condition as well.

If a patient exhibits one event, it may be desirable to turn on internally of the device several Holter monitor and memory functions that enable a more exact therapy to be delivered by the device according to the more tailored analysis of the patient's needs, and to program the device accordingly. As noted above, a cardiac patient cannot easily tolerate the physical, mental, emotional, and economic toll of multiple operations which may range from an initial relatively simple implant device to successively more complex devices to meet the advancing needs for therapy dictated by progressive heart disease. The additional mortality and morbidity concerns upon the patient with repeated surgery could be devastating. Added to this is the care required to be delivered to this patient by the physician, surgical, and hospital services, and, where care may be limited by government-imposed cost containment mandates, as it is with the very patients of advanced years who generally have need for such implant devices, the situation becomes particularly difficult.

It is therefore another important aim of the present invention to provide an implantable full featured medical device which is capable of delivering a full range of pacing, cardioversion, and defibrillation therapies from the patient's needs at the onset of the disease, and through the likely progressively more serious events that occur with advancing age. According to the invention, the device is programmed and reprogrammed only as and to the extent that it becomes necessary to meet those needs when and as they may arise. Although the device is full featured, the patient (or third party payor, if applicable) need make no initial financial outlay for the device itself beyond that required to cover the pricing for those features of the device which are made available at the time of implant, i.e., the therapy(ies) programmed for potential delivery to the implant patient to treat episodes of the diagnosed arrhythmia(s) for which treatment is currently prescribed. Thereafter, additional device charges will be imposed only to the extent that additional features are required to treat specific manifestations of an advancing disease or new disorder, and are actually programmed into the device. Accordingly, the patient's account is not addressed for features which, though available within the device itself by proper programming, are presently unused and not a part of the therapy which has been provided by the device to date.

Initially, then, the device need merely be made capable of performing the basic therapeutic needs required by the patient, in addition to delivering a life saving shock. The basic needs may, for example, include or be limited to the delivery of a pacing function for a slow heart rate in response to detection of the need for such therapy. But the device possesses the further capability to be adjusted later to meet additional needs of the patient with the passage of time—importantly, without a requirement for additional surgical procedures for replacement of the device. Thus, the solution to the problem is that initially the implanted device is provided with very basic features from among those that it is capable of delivering. However, the device possesses means that enable it to be upgraded non-invasively and successively, whenever the requirement exists for additional therapy(ies) to be delivered to meet the patient's additional needs. In essence, this means that the hardware and software routines for the full range of initial and additional intelligent functions is present in the device, but the software control parameters necessary to configure the final functionality are programmed into the device at a later time if, as and when the need arises. And although allowing access to previously restricted software and hardware features will be subject to payment of an additional amount appropriate to the new feature(s) which are made available as additional therapy to the patient, by way of a non-invasive upgrading of the implanted device, the cost will be substantially lower than would otherwise be the case if multiple, successive surgical procedures were required for device and lead replacements.

A serious problem encountered in the use of such an upgradable device, however, resides in the manner in which safeguards will be employed to preclude access to externally programmable software control registers and, thus, for upgrading—or indeed, in any way modifying—the features of the implanted device by anyone other than an authorized person. In general, the authorized person is the patient's attending cardiologist. To that end, the device is encoded in a suitable manner to lock it against access to those of its internal programs which relate to upgrades, i.e., the addition (or even selective removal) of therapies, except to an authorized person in possession of a key to unlock the access—generally, the physician. The key(s) to unlocking the code are supplied by the manufacturer of the device. Alternatively, the necessary programming changes might be made from time to time by the manufacturer, such as by modem, when called upon to do so by, and in consultation with, the patient's physician. In any event, certain functions which have customarily been made programmable in conventional implanted devices to allow changes, selections, activation, or deactivation by the physician (or in some case, by the patient, as well) would not be affected. That is, programming those functions would continue to be handled in the same manner as before, without need for the special codes or keys that mark the security for an upgradable device.

According to a further aspect of the present invention, the upgrading is performed by identifying the serial number of the device to allow a certain code to be addressed by programmer software. For example, to allow a very fast upgrade of a patient's device, the upgrade data may be through a service of the device manufacturer delivered by key file via Internet, E-mail, or telephone modem transfer, or any other communication means presently available or subsequently developed, so that the device can be programmed with additional software information and that additional functions, otherwise dormant (through blocking) but available, in the device can be activated. By this means, the additional cost of the full, more complex device will be saved at the outset for those patients who require only selected basic ones of the features built into the device—and who are not primarily identified as candidates for sudden cardiac death but are only at risk without ever going into ventricular fibrillation, and in whom there is no actual need to bear the cost of the more expensive and complex (i.e., full featured) device at that time but for whom the basic device will suffice for the present.

Thus, the cost of a basic device in current dollars could be reduced to less than $10,000, while the additional upgrade might cost another $8,000-10,000, in comparison to a typical cost of $15,000 for a basic function defibrillator device and a cost of $20,000 for a typical upgrade replacement unit.

A further aspect of the present invention is the provision of a graded upgrade —which means that certain functions such as Holter monitor-type, or certain pacing functions such as antitachycardia pacing functions, extended memories, and so on can be turned on and activated individually depending on how much the physician determines to be needed for a particular patient. The reimbursement cost and any additional cost to activate the device in this manner are based on the amount of additional intelligence and service required for the activated, upgraded unit as implanted.

BRIEF DESCRIPTION OF THE DRAWINGS

The above and still further aims, objects, aspects, features and attendant advantages of the present invention will become apparent from a consideration of the following detailed description of the presently contemplated best mode of practicing the invention, by reference to a preferred embodiment and method, taken in conjunction with the accompanying drawings, in which:

FIG. 4, parts A, B, and C, are functional block diagrams useful in further explaining the preferred embodiment of a device implemented according to the invention, and the preferred method of providing arrhythmia therapy using the device.

DETAILED DESCRIPTION OF THE PREFERRED EMBODIMENT AND OF THE INVENTION

Figure 1:
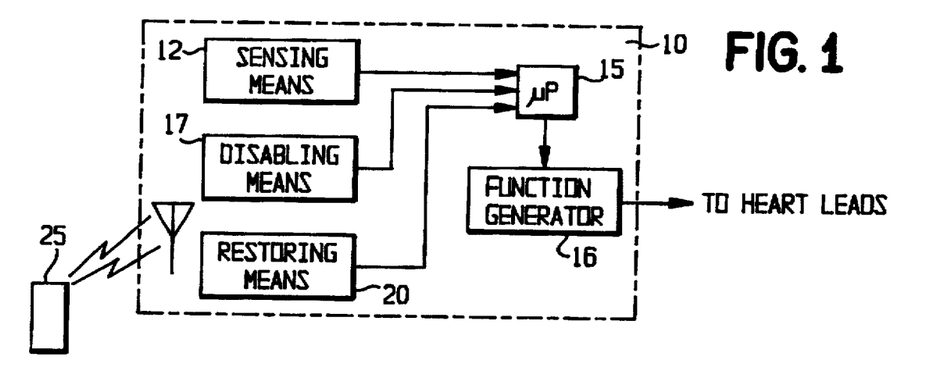
FIG. 1 is a block diagram of an exemplary embodiment of the presently-contemplated best mode of practicing the invention, in the form of an implantable cardioverter/ defibrillator device.

FIG. 1 is a block diagram of an exemplary embodiment of the invention, in the form of an implantable cardioverter/ defibrillator device 10, all of the components of which may be entirely conventional except as otherwise described herein. Device 10 is constructed and adapted, according to the principles of the invention, to be upgraded from time to time. The upgrading is to be performed as may be necessary to enable the device to provide additional therapy for treatment of arrhythmias in a patient (not shown) in whom the device is to be implanted, as the needs of the patient for such treatment undergo change with the passage of time.

Device 10 includes a function generator 16 which constitutes means for providing a plurality of functions corresponding to different levels of therapy for treatment of arrhythmias. The function generator may be of known construction to generate various types of relatively low energy pulse waveforms for pacing therapy such as antitachycardia pacing, moderate energy cardioverting shock waveforms for cardioversion therapy, and relatively higher energy defibrillating shock waveforms for defibrillation therapy, as well as any other arrhythmia treatment signals. Function generator 16 may, and generally will, include an output circuit (not shown) for delivering the designated therapy to the appropriate set of heart leads and electrodes. In particular, the output circuit may include capacitors and high voltage switches that enable the higher energy defibrillating shocks to be applied to electrodes that will establish the necessary electric field through the mass of the heart encompassing the chambers (e.g., the ventricles) which are to be defibrillated. The electrodes used for applying the various electrical waveforms for arrhythmia therapy may include the biocompatible metal housing (i.e., the case, or "can") of device 10 itself—the housing being indicated by the dotted lines in the Figure—as an active electrode, if desired for a particular type of therapy.

The function generator 16 performs its therapy-generating and delivery functions under the control of a microprocessor or microcontroller 15 which is a single-chip (semiconductor integrated circuit) system containing arithmetic, logic, and control circuitry for general purpose data processing or computing, and operating in conjunction with on- or off-chip peripheral circuits or subsystems such as memory, clock, and so forth, to constitute a central processing unit (CPU) for the device. Microprocessor 15 is sufficiently powerful to respond to a multiplicity of pre-programmed or programming instructions to perform high speed, real-time functions by which to control the operation of function generator 16. The on-chip or off-chip memory (typically, electrically programmable read-only memory, or EPROM, not shown) may be programmed, and together with the capability of separate telemetry programming from a program console through a wand 25, and related software or firmware, allows the microprocessor to perform functions which may be varied by means of a programming unit, or programmer, such as by the device manufacturer or the patient's attending physician.

A sensing means 12 is provided to detect various physiologic parameters indicative of the patient's cardiac functions and physical status, so as to sense different types of arrhythmias and initiate appropriate response mechanisms from the device. For example, the sensing means may be located within the device 10 housing, as shown, or outside the device in its own implanted housing (not shown), or in some instances, even external to the patient, or partly inside and partly outside the device 10 housing. The sensing means is preferably capable of detecting the patient's electrogram (ECG) and supplying signals indicative of functions including heart rate and rhythm, as well as parameters indicative of exercise or activity of the patient, so that the device 10 may provide a rate adaptive response to the status of patient activity as well as to perform the other arrhythmia correction therapies which have been mentioned. Signals generated by the sensing means 12 are converted to digital form and supplied to the microprocessor 15 to modulate the performance of the latter and its control over the operation of the function generator 16.

The microprocessor 15 responds to each different type of arrhythmia sensed by sensing means 12 (as well as to other relevant physiologic parameters detected by the sensing means, such as patient activity) for enabling the function generator 16 to provide a functional output waveform which is appropriate to correct or otherwise treat the respective sensed arrhythmia. Some of these functional output waveforms may be used without change for application to several different types of arrhythmias. For example, a burst of pulses may be generated as a therapy to terminate a tachycardia, and may also be one among a hierarchy of responses which are selectively delivered in a cardioversion program.

When no immediate demand for therapy is being imposed upon device 10, the microprocessor may revert to a "sleep" mode, subject to be awakened at any time that a therapy requirement is indicated, such as by the sense signals.

According to the invention, means 17 are provided for programmably disabling at least some of the several, or plurality of, functions that may be delivered by device 10 by virtue of the operation of the components including microprocessor 15 and function generator 16. That is, the device 10 is implemented to provide a variety of therapies as has just been described (i.e., is a "full featured" device), and as may be found in any number of prior art medical devices for treating cardiac arrhythmias. However, the device 10 is also provided with a means by which its capability to deliver all of the functions is curtailed, but is nevertheless sufficient to address the present needs and demands of the patient in which it is, or is to be, implanted. For example, if the patient is experiencing sporadic tachyarrhythmias, but no other manifestations of cardiac disease or defect, the device may be programmed to deliver an anti-tachy therapy—which may include a number of different treatment waveforms that are delivered in a sequence ranging from a conservative response to an aggressive response, but restricted to that malady. The patient has the full featured device implanted, but programmed only with the anti-tachy therapy.

Of course, the implant might instead have been a device which was manufactured to provide only that identical anti-tachy therapy, and with no capability whatsoever to be upgraded to provide any other or any additional therapy. In that case, however, the patient (or third party payor, whether insurance carrier or otherwise) would find substantially the same charge imposed—for the device, and the surgical procedure to implant (except for any differences that might be attributable to implant location, and nature and number of heart leads required to be implanted)—as would be the case if the full featured device 10 had been implanted. More significantly, in the former case, if the patient began suffering other manifestations of progressive heart disease that might require occasional or even frequent cardioversion or defibrillation, it would be necessary to explant the current device, and to implant a suitable replacement capable of addressing these events. Aside from the additional cost of a completely new device and the surgery required to implant it, the patient would be subjected to the trauma and risk associated with the new surgery no matter how much it might be viewed by the physician as being relatively simple or routine.

In contrast, device 10 further includes means 20 for selectively restoring the disabled functions, which preferably also includes security means for encoding the device to preclude the restoration of disabled functions (or any other modification of device features), except by an authorized entity. In the preferred embodiment, the security means is implemented to require participation by both the attending physician and the device manufacturer to effect an upgrade. Hence, if the upgradable device 10 is implanted, the patient's need for additional features attributable to progressive heart disease is readily accommodated by simply programming the implanted device to upgrade its features accordingly.

Despite this capability to modify the capabilities (features) of an implanted medical device, certain concerns arise for an upgradable device of the kind described herein. Since a medical device 10 which is full featured possesses at least some features that put it in the category of a life-saving device, it is important that the device should be sufficiently secure that it is virtually incorruptible. To that end, device 10 is provided with a security system to prevent it from being reprogrammed without an appropriate key or keys, which will be described presently.

In addition, it is important that the upgradable device should not be recognized by existing applications in the field. This means that no interference or override should occur through existing or future programming or device operation which is or will be available from the device manufacturer. Each upgradable device should have its own unique personal identification code, or identifier (ID), which should be embedded in the device in nonvolatile memory so that it will not be erased in the event of a loss of electrical power to the device (which, of course, is provided by battery).

A compatibility determination check (i.e., to assure compatibility between the upgradable device and the external programmer, particularly with respect to software of each) may be performed by retrieving or verifying the nonvolatile ID (which may, for example, be the serial number of the device) plus a volatile ID (which may, for example, be the model number of the device). The latter ID is embedded in programmable memory to allow it to be reprogrammed in the event of corruption. In addition to these ID's, a data memory of the device has a location which identifies the level at which the device is currently upgraded (i.e., the enabled features), based on the state of the device software. Thus, the upgrade level may be read at any time by the attending physician to verify the current status of the device; and may be written to in order to reprogram the device to a new upgrade level. An error detection code is provided, which can be read to detect errors, and written to correct errors. These techniques are provided or performed in a conventional manner, the uniqueness residing in the purpose for which they are used.

Also, in the preferred embodiment, the device is implemented with a backup reset feature. In the preferred version, the device is reset to a full-featured device (from a partial-featured mode), but requires programming of the authorized upgrade codes at a later date for all features to remain active. Alternatively, the device may be reset to a predetermined limited functional mode, and the user prompted to obtain upgrade codes from the manufacturer. Both options will allow instantaneous restoration of critical feature for patient safety, while preventing unauthorized upgrading of the device.

Only the minimum life saving functions or features, such as defibrillation shock and bradycardia backup pacing need be restored by a reset module. Additional features could be upgraded with special access module programming.

Figure 2:
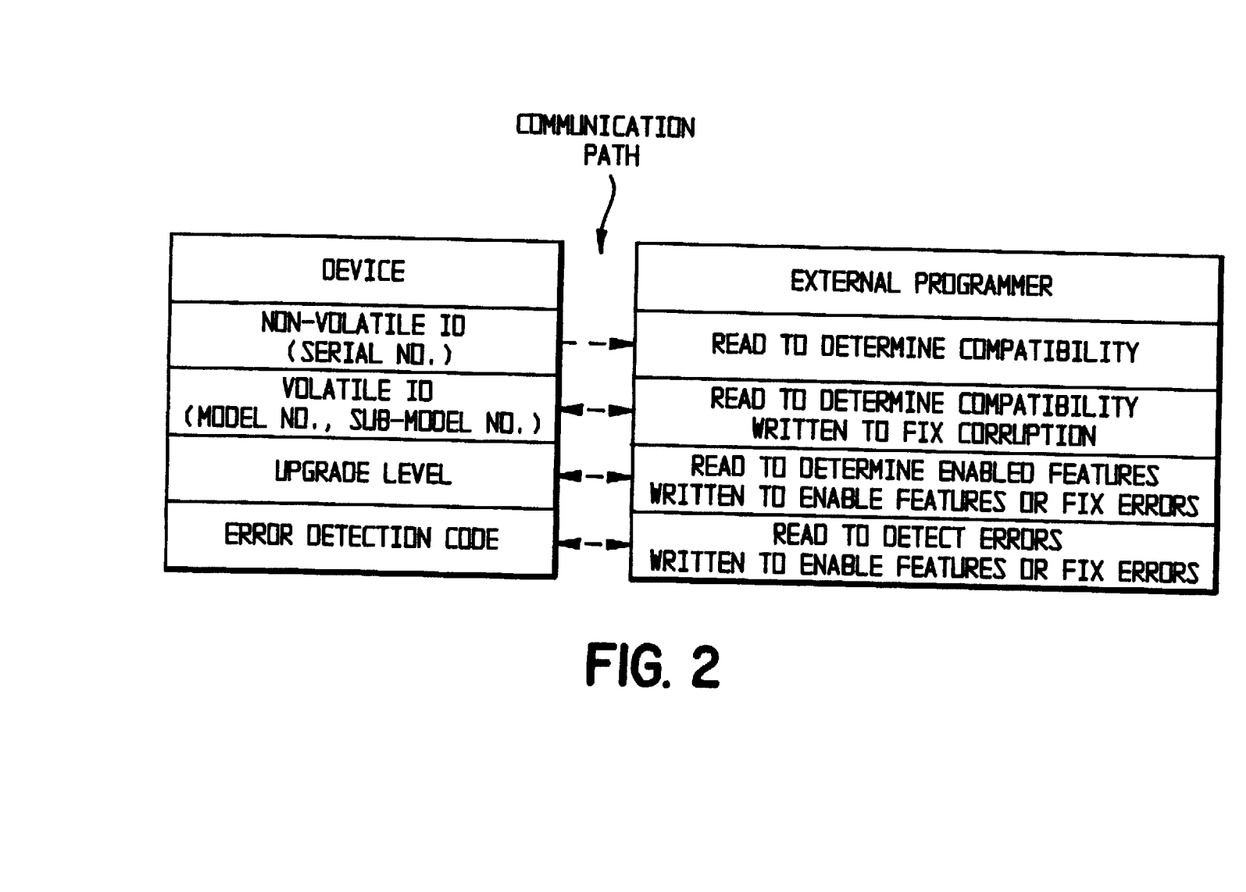
FIG. 2 is a chart of characteristics for the device of FIG. 1, and capabilities of an external programmer for reading and programming memory associated with the device.

Such capabilities are illustrated, for the preferred embodiment, in the chart of FIG. 2. The device 10 characteristics are on the left, the external programer (with wand 25) is on the right, and the communication direction is illustrated by the lines and arrows between the two. All of the listed characteristics or parameters for the device are stored in read-only memory (ROM) and random access memory (RAM) associated with the device. The device software supports the full range of features available with all combinations of upgrades. The external programmer uses the volatile control parameters of the device software to enable, disable, or limit the range of features according to the selected upgrade level.

Figure 3:
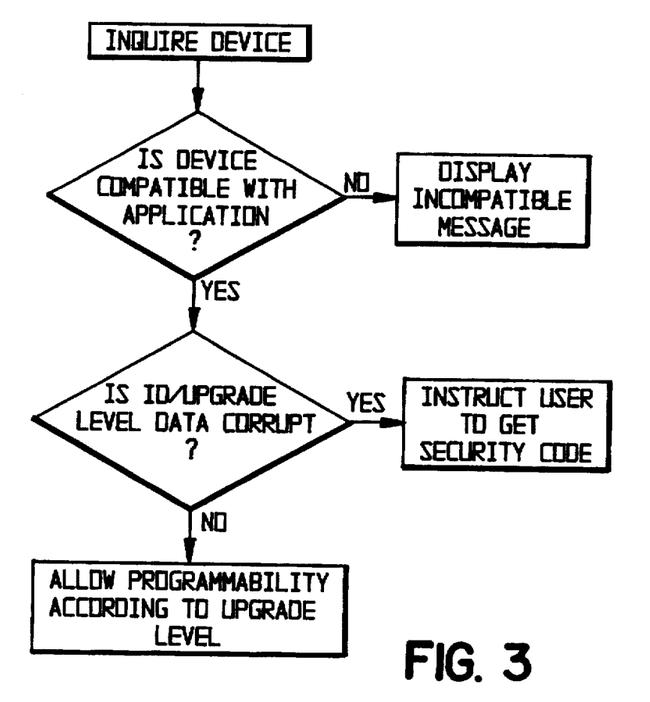
FIG. 3 is a flow diagram for the external programmer application software.

A flow diagram for the external programmer application software is illustrated in FIG. 3. An inquiry is made to the device from the external programmer (the programming console) to read the device 1D and to determine therefrom the compatibility of the device with the application software of the external programmer. If compatibility does not exist, a flag or message is displayed to that effect on a display of the programmer. But if the two are compatible, a further test is made to determine whether the ID/upgrade level data are corrupt. If any of the data is corrupt, the user (physician) is instructed to get the security code. Otherwise, the user is notified (also on the display) that programming is permitted to the extent of the upgrade level. Certain of the features may be limited in range or availability.

Figure 4A:
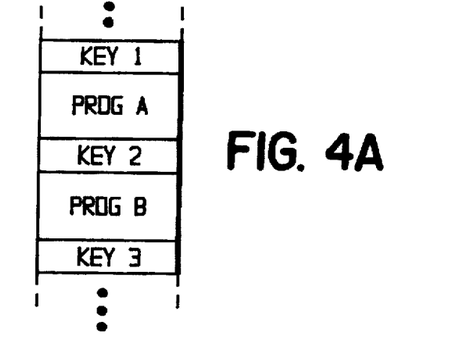
Figure 4B:
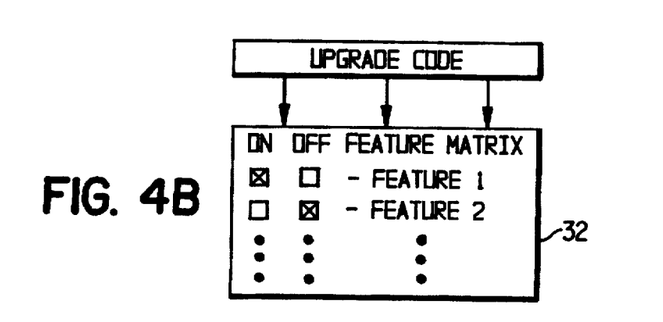
Figure 4C:
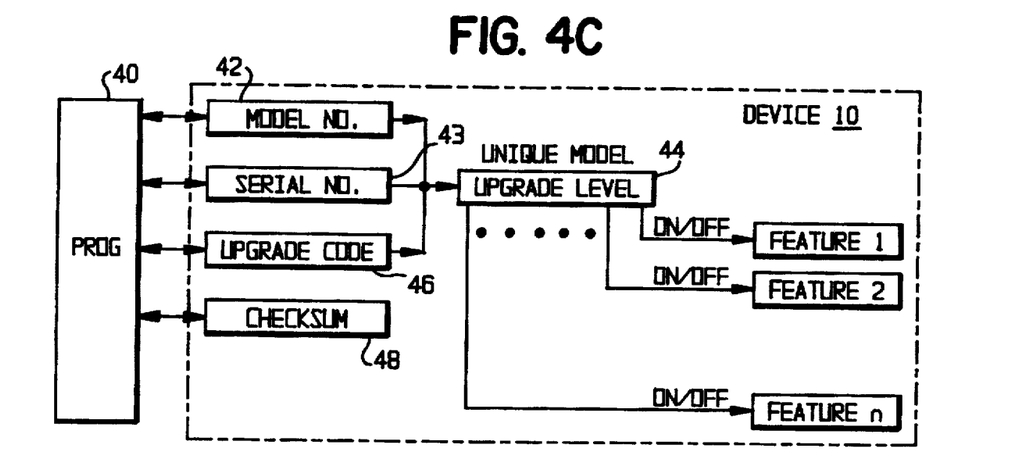

In FIG. 4, parts A, B, and C illustrate aspects of the control over features of the device by the external programmer. In FIG. 4A, a security code constituting a key (e.g., key 1, key 2, key 3, etc.) is required to unlock each program and the feature associated with the respective program. According to the preferred embodiment, the appropriate key (security code) in each instance is supplied by the device manufacturer, upon notification from the attending physician for the implant patient that the device is to be reprogrammed to modify the original feature or a subsequently upgraded version to meet the patient's current needs for cardiac arrhythmia therapy. As has been explained above, the modification can be accomplished on a non-invasive basis by simply applying the new programming to the implanted device through the external programmer and telemetry after the key has been provided. By safeguarding the key, the manufacturer is assured of being notified before any adjustment can be made to the features of the device. A charge may then be imposed for the additional feature(s), or the upgrade, to compensate the device manufacturer for the original implementation. The cost to the patient, however, is considerably less than would have been the case had the implanted device required replacement, and the risk and trauma to the patient are substantially eliminated.

In FIG. 4B, the status of each feature is controlled by the upgrade code, which includes the respective key and the program for that upgrade/feature. For example, as shown, a feature 1 is programmed "on", while a feature 2 is disabled to be "off". Other features may be left or restored to be "on" or disabled to be "off" as necessary to provide the device capabilities that will meet the needs of the patient. A display 32 may be provided on the programmer monitor to show the feature matrix as currently programmed. An upgrade code (another key) is applied in FIG. 4B to enable (or restore) feature 1, while leaving feature 2 disabled.

In FIG. 4C, the external programmer 40 interrogates the device 10 for model number (at 42) and serial number (at 43), and, if the response indicates that the compatibility is positive, checks the upgrade level (at 44) of the device and applies an upgrade code (at 46, to manage the availability of certain features defined by sections of the software, by restricting or allowing access with software keys) for installing (restoring) the additional features required according to the patient's condition. A check sum is performed by the programmer (at 48) to detect and correct errors. Having unlocked a feature or features with the applicable key, those unlocked features among 1, 2, . . . N, may be programmed or restored as necessary to provide the features (the therapies) required to treat the patient's cardiac arrhythmias as prescribed by the attending physician.

In the preferred embodiment, the upgrade information is stored in software or semiconductor memory in the device, and is encoded to deter intentional alteration. This is accomplished preferably by storing a value which is a complex mathematical combination of the upgrade level, the device model number, and the device serial number, so that the upgrade level value stored is then unique for each device.

This upgrade information, along with the model and serial number information for the device, is protected by an error detection code. In the preferred embodiment, this error detection code is a checksum, which will allow the application program to recognize alteration or corruption of the serial number or the upgrade level. When an error is detected, the application displays the serial number and upgrade level correction screen on the console, to prompt the user to contact the manufacturer for a security code.

Preferably, the upgradable device is adapted from an existing conventional device design, with customized programmer software architectures that minimize modifications to existing conventional programmer application code and device code. The graded upgrading may apply to each individual function of the device, so that each such function when programmed into the device carries with it a particular imposition of a charge to the patient's account. Such charges would be imposed for each new function until the device is made fully operational, i.e., the full range of its features are made available to the patient. Additional charge would apply, for example, to the provision of extended memory, VVIR pacing (rate adaptive), VDD pacing, anti-tachycardia pacing, atrial defibrillation, programmable polarity of the shock, programmable impulse characteristics of the shock, and other diagnostic and therapeutic features.

From the above description, it will be appreciated that the present invention goes beyond the use of an external programmer to provide data to preselected registers and RAM memory locations within an implanted medical device, such as a pacemaker or defibrillator, which affect either the sections of software routines to be executed or the parameters to be used in that execution. The invention represents an enhancement extending to a method and system of managing the availability of certain sections of the software which constitute operational features of the device by restricting or allowing access to those features (through the applicable sections of the software) by means of software keys.

Thus, although a presently contemplated best mode of practicing the invention has been described herein, it will be recognized by those skilled in the art to which the invention pertains from a consideration of the foregoing description, that variations and modifications may be made without departing from the true spirit and scope of the invention. Accordingly, it is intended that the invention shall be limited only by the appended claims and the rules and principles of applicable law.

What is claimed is:

1. An implantable cardioverter/defibrillator device adapted to be upgraded from time to time to enable the device to provide additional therapy for treatment of dysrhythmias in a patient in whom the device is implanted, as the needs of the patient for such treatment undergo change, said device comprising means for providing a plurality of functions corresponding to different levels of therapy for treatment of dysrhythmias; means for sensing different types of dysrhythmias; means responsive to each different type of dysrhythmia sensed by said sensing means for enabling said function providing means to provide a level of therapy appropriate to the respective sensed dysrhythmia; means for programmably disabling at least some of said plurality of functions; means for selectively restoring the disabled functions; and means for precluding the restoration of disabled functions except upon access through a security code.

2. An implantable medical device for arrhythmia detection and correction, adapted to provide a plurality of different therapies in the form of various corresponding electrical waveform functions for application to the heart to treat a wide range of respective arrhythmias including bradycardia, tachycardia, and fibrillation, said device including function generating means for selectively generating electrical waveform functions corresponding to said plurality of different therapies in response to detection of respective ones among said wide range of arrhythmias; means for disabling said function generating means from generating at least some of said electrical waveform functions based on absence of need for all of said plurality of different therapies by the patient receiving the device as an implant; and means for programmably restoring the capability of said function generating means to generate selected ones of said at least some electrical waveform functions for which it was previously disabled when the patient evidences a need for additional therapy corresponding thereto; said device further including means to lock out operation of the programmable restoring means except with a prescribed key.

3. A method for selectively non-invasively upgrading an implanted cardioverter/defibrillator device from time to time to enable the device to provide additional therapy for arrhythmia treatment in the implant patient, as the needs of the patient for such treatment undergo change, said method comprising the steps of:

providing a plurality of functions corresponding to different levels of therapy for treating arrhythmias;

sensing different types of arrhythmias;

responding to each different type of arrhythmia sensed for supplying a function appropriate to relieve the respective sensed arrhythmia;

initially restricting the device from providing at least some of said plurality of functions as being nonessential to the patient's needs; and selectively restoring restricted functions of the device only with the aid of a code substantially unique to said device, as the patient experiences need for additional therapy.

4. A method for arrhythmia detection and correction using a non-invasively upgradable universal implanted medical device, which comprises the steps of:

providing said device with the capability to generate a plurality of different therapies in the form of various corresponding electrical waveform functions for application to a patient's heart to treat a wide range of respective arrhythmias including bradycardia, tachycardia, and fibrillation;

enabling said device to generate only selected ones of said electrical waveform functions at the time of initial implant of the device into a patient, according to a then-current diagnosis of the patient's arrhythmia; and further enabling said device non-invasively from a point external to the patient to generate selected others of said electrical waveform functions from time to time thereafter as the patient evidences a need for additional or different therapy, subject to first delivering by telemetry to the device an enabling code unique to the implanted device.

5. The method of claim 4, wherein the step of further enabling said device to generate selected other waveform functions includes detecting said enabling code as a key to unlock a capability of said device to generate said other waveform functions.

6. The method of claim 5, further including the step of obtaining said enabling code as a key from the device manufacturer.

7. The method of claim 6, wherein the step of obtaining includes selectively obtaining any of a plurality of enabling codes, each enabling code being unique to the implanted device and each being associated with a respective set of one or more of said other waveform functions.

8. The method of claim 6, wherein the step of obtaining includes selectively obtaining a predetermined one of said plurality of enabling codes which is both unique to the particular implanted device and associated with unlocking the capability of said device to generate a particular desired one of said other waveform functions.

9. An implantable cardioverter/defibrillator device adapted for universal use in treating a plurality of different dysrhythmias among those which might be suffered by individuals among a wide group of cardiac patients in whom the device is to be implanted, said device comprising a function generator for generating a plurality of therapeutic electrical waveforms, each of which is to be applied selectively to the patient's heart to treat a particular one or more but less than all of said plurality of dysrhythmias when said particular one or more dysrhythmias is detected; means for programmably enabling and disabling said plurality of therapeutic electrical waveforms to establish a mix thereof conforming to a schedule of those dysrhythmias which are to be treated and those which are not to be treated by said device at the time of implant thereof, among said plurality of different dyshythmias; and means for selectively varying the mix of enabled and disabled waveforms among said plurality of therapeutic electrical waveforms generated by said function generator to conform to a new schedule of dysrhythmias to be treated and not treated among said plurality of different dysrhythmias, wherein said means for selectively varying the mix includes means for rendering said selective variation of mix operational only in response to a predetermined unique security code.

10. The device of claim 9, wherein said means for rendering is responsive to a plurality of distinct and different security codes which are unique to the particular implanted device.

11. The device of claim 10, wherein each of said distinct and different security codes is a code supplied by the manufacturer of the implanted device.

12. The device of claim 11, wherein each of said distinct and different security codes is a code associated with a respective distinct and different mix of enabled and disabled waveforms, so that once a particular mix is selected, the same code which permitted such selection cannot be used for selecting a different mix.

13. A method of non-invasively selecting treatment of a particular dysrhythmia by an implantable cardioverter/defibrillator device adapted for universal use in treating a plurality of different dysrhythmias among those which might be suffered by individuals among a wide group of cardiac patients in whom the device is to be implanted, said device comprising a programmable function generator for generating a plurality of therapeutic electrical waveforms, each of which is to be applied selectively to the patient's heart to treat a particular one or more but less than all of said plurality of dysrhythmias when said particular one or more dysrhythmias is detected; said method comprising the steps of:

programmably enabling and disabling said plurality of therapeutic electrical waveforms generated by said function generator to establish a mix thereof conforming to a schedule of those dysrhythmias which are to be treated and those which are not to be treated by said device at the time of implant thereof, among said plurality of different dyshythmias; and if the device is to be used for treating a new schedule of dysrhythmias, selectively varying the mix of enabled and disabled waveforms among said plurality of therapeutic electrical waveforms generated by said function generator to conform to the new schedule of dysrhythmias to be treated and not treated among said plurality of different dysrhythmias, including permitting the selective variation of mix only upon presentation of a predetermined unique security code.

14. The method of claim 13, wherein the step of permitting said selective variation of mix comprises responding therefor to any of a plurality of distinct and different security codes which are unique to the particular implanted device.

15. The method of claim 14, further including obtaining each of said plurality of distinct and different security codes from the device manufacturer.

16. The method of claim 15, wherein each of the codes among said plurality of distinct and different security codes to be obtained from the device manufacturer is associated with a respective distinct and different mix of enabled and disabled waveforms, so that once a particular mix is selected, the same code which permitted such selection cannot be used for selecting a different mix.

* * * * *